US006554768B1

(12) United States Patent
Leonard (10) Patent No.: US 6,554,768 B1
(45) Date of Patent: Apr. 29, 2003

(54) ILLUMINATED DEEP PELVIC RETRACTOR (75) Inventor: Robert F. Leonard, Suwanee, GA (US)

(73) Assignee: Genzyme Corporation, Cambridge, MA (US)

( * ) Notice: Subject to any disclaimer, the term of this patent is extended or adjusted under 35 U.S.C. 154(b) by 271 days.

(21) Appl. No.: 09/656,932

(22) Filed: Sep. 5, 2000

(51) Int. Cl.⁷ ............................................. A61B 17/00
(52) U.S. Cl. ...................... 600/213; 600/210; 600/226; 600/235; 600/245; 600/246
(58) Field of Search ................. 600/210, 213, 600/235, 245, 246, 226, 201, 212, 214

(56) References Cited

U.S. PATENT DOCUMENTS

| | | | |
|---|---|---|---|
| 4,052,980 A | 10/1977 | Grams et al. | |
| 4,562,832 A | 1/1986 | Wilder et al. | |
| 4,597,030 A | 6/1986 | Brody et al. | .................. 362/32 |
| 4,765,701 A | 8/1988 | Cheslak | |
| 4,934,352 A | 6/1990 | Sullivan, Jr. | |
| 4,996,976 A | 3/1991 | Nakagawa | |
| 5,005,108 A | 4/1991 | Pristash et al. | ................ 362/31 |
| 5,035,232 A | 7/1991 | Lutze et al. | |
| 5,351,680 A | 10/1994 | Jung | |
| 5,503,617 A | 4/1996 | Jako | ............... 600/201 |
| 5,514,076 A | 5/1996 | Ley | ................ 600/206 |
| 5,514,077 A | 5/1996 | Rabban | ....................... 600/226 |
| 5,667,480 A | 9/1997 | Knight et al. | ................ 600/210 |
| 5,722,934 A | 3/1998 | Knight et al. | |
| 5,725,479 A | 3/1998 | Knight et al. | ................ 600/210 |
| 5,730,748 A | 3/1998 | Fogarty et al. | ............. 606/159 |
| 5,776,159 A | 7/1998 | Young | ......................... 606/190 |
| 5,797,947 A | 8/1998 | Mollenauer | .................. 606/192 |
| 5,827,318 A | 10/1998 | Bonutti | ....................... 606/190 |
| 5,846,191 A | * 12/1998 | Wells et al. | ................ 600/201 |
| 5,853,417 A | 12/1998 | Fogarty et al. | ............. 606/159 |
| 5,902,233 A | * 5/1999 | Farley et al. | ................ 600/213 |
| 5,904,650 A | 5/1999 | Wells | .......................... 600/226 |

(List continued on next page.)

FOREIGN PATENT DOCUMENTS

| | | |
|---|---|---|
| GB | 2078526 | 1/1982 |
| WO | WO 99/01696 | 1/1999 |
| WO | WO 99/52449 | 10/1999 |
| WO | WO 99/56633 | 11/1999 |

OTHER PUBLICATIONS

Auto Suture Company, The Mini–Harvest System for Minimally Invasive Saphenous Vein Harvesting, 1996.

Design News, Medical Plastic/Cover Story, Bypass Surgery Made Easier, Disposable Instruments, made from standard plastics, key to minimally invasive procedure for extracting veins, Gary Chamberlain, Senior Editor, pp. 57–58; 60, 62 (Jan. 6, 1997).

Dimitri, W. R. et al., A Quick and Atraumatic Method of Autologous Vein Harvesting Using the Subcutaneous Extraluminal Dissector, J. Cardiovasc. Surg., vol. 28, pp. 103–111 (1987).

(List continued on next page.)

Primary Examiner—Cary E. O'Connor
(74) Attorney, Agent, or Firm—Richard D. Allison; Thomas J. DesRosier (57) ABSTRACT

An illuminated deep pelvic surgical retractor for illuminating a surgical site and retracting tissue adjacent thereto, the illuminated surgical retractor having a handle member interconnected at an obtuse angle to a first elongate section and a second elongate section that is releasably connected to the first elongate section and a portion of the second elongate section defining an illumination input end portion which is optically coupled to a light source so that the second elongate section is substantially illuminated, and, a shield member is positioned adjacent to the distal end portion of the first elongate section to aid in directing light selectively from the second elongate section to the desired tissue or organ.

30 Claims, 5 Drawing Sheets

U.S. PATENT DOCUMENTS

| | | | | |
|---|---|---|---|---|
| 5,913,818 | A | 6/1999 | Co et al. | 600/204 |
| 5,921,919 | A | 7/1999 | Chin et al. | 600/217 |
| 5,967,971 | A | 10/1999 | Bolser | 600/211 |
| 6,033,361 | A | 3/2000 | Co et al. | 600/210 |
| 6,228,025 | B1 * | 5/2001 | Hipps et al. | 600/245 |
| 6,350,236 | B1 * | 2/2002 | Hipps et al. | 600/213 |

OTHER PUBLICATIONS

Dregelid, E. et al., Endothelial Cell Injury in Human Saphenous Veins After Manipulation and Tweezer Grasping, J. Cardiovasc. Surg., vol. 29, pp. 464–469 (1988).

Gundry, Steven R., et al., Optimal Preparation Techniques for Human Saphenous Vein Grafts, Surgery, No. 6, pp. 785–794 (Dec. 1980).

Hauer, G. et al., Endoscopic Subfascial Discission of Perforating Veins, Surg. Endosc., vol. 2, pp. 5–12 (1988).

Lee, John, Surgical Physician Assistant, Minimally Invasive Vein Harvesting, Nov./Dec. 1996, pp. 26–32.

Meldrum–Hanna, W. et al., Long Saphenous Vein Harvesting, Aust. N.Z. J. Surg., vol. 56, pp. 923–924 (1986).

Moazami, Nader et al., Minimally Invasive Greater Saphenous Vein Harvesting for Coronary Artery Bypass Surgery, Surgical Rounds, pp. 94–97 (Mar. 1997).

Rashid, A. et al., Subcutaneous Technique for Saphenous Vein Harvest, The Annals of Thoracic Surgery, vol. 37, No. 2, pp. 169–170 IFeb. 1984).

Snowden Pencer DSP, The Diamond–Line of Surgical Instruments Brochure, Tebbetts EndoPlastic Instrument System, 1995.

Snowden Pencer DSP, EndoCABG System, Innovative Instrumentation for Endoscopic Coronary Artery Bypass Grafting, 1996.

Wheatley, D.J.,Autocronary Bypass Grafting Techniques, Surgery of Coronary Artery Disease, pp. 348–349 (Date Unknown).

* cited by examiner

ILLUMINATED DEEP PELVIC RETRACTOR

FIELD OF THE INVENTION

The present invention relates, in general, to a surgical retractor and, in particular, to a new and useful illuminated retractor for creating a working space for dissecting instruments in support of a surgical procedure such as a procedure for performing surgery in the pelvic area of a patient or other types of procedures which require the retraction of tissue at a relatively deep location in the body of a patient.

The present application is with U.S. Ser. No. 09/071,786 filed on May 1, 1998 now U.S. Pat. No. 6,228,025 and both applications are commonly assigned to the assignee of the present application.

BACKGROUND OF THE INVENTION

In certain surgical procedures, such as abdominal or gynecological reconstruction or resection procedures, it is necessary to retract tissue at a relatively deep location in the body of a patient. In these surgical procedures, it is also necessary to remove or retract a portion of tissue or an organ in a patient during the procedure. Various specialized retractors are available and although they provide the physician with access to the desired tissue, a separate source of illumination is often required. Common examples of these deep pelvic types of surgical procedures include, pelvic floor reconstruction, vaginal vault reconstruction, prostatectomy, anal resection, abdominal perianal resection and low anterior resection procedures.

In a deep pelvic procedure, it is important to provide reliable access to the desired tissue by retracting the tissue around the surgical site. Once this tissue is retracted, it is important to retain the tissue or organ out of the surgical site during the entire procedure. Therefore, a St. Mark's style retractor is currently available to provide access to the desired tissue. A St. Mark's style retractor consists generally of an elongate flat member with a perpendicularly extending bottom surface and a perpendicularly extending top surface and a handle that is attached to the perpendicularly extending top surface. Currently, the physician must use a separate light source such as a head-mounted light or a separate lighted instrument to illuminate the head-mounted light is used and the surgical site is located deep within the body of the patient, it is often difficult to view the desired tissue without shadows from the adjacent tissue. Because the available tissue opening is relatively limited, it is desirable that the number and size of instruments be kept to a minimum. It is also desirable to provide a source of light inside the retracted tissue area to illuminate the tissue of interest without obstructing the view of the surgeon.

The present invention overcomes the drawbacks of limited movement and limited workspace created by the use of the presently available surgical instrumentation and the limited and distorted visual perspective provided by the use of a separate source of illumination. It is therefore desirable to provide a means of providing illumination to the surgical space formed by the retractor so that the physician and physician's assistant can efficiently view and operate in the entire surgical field exposed by the retractor.

SUMMARY OF THE INVENTION

The present invention overcomes the disadvantages of the prior art. As shown in the drawings, the present invention provides an illuminated retractor for illuminating the surgical field from a location along the side of the surgical field.

The illuminated retractor provides a large, well illuminated surgical field, which preferably extends the substantial length of the retractor within the surgical space created by the retractor and further includes a shielded area to prevent the illumination from shining into the eyes of the physician or physician's assistant.

The illuminated surgical retractor preferably has a handle member, a first elongate section and a second elongate section. The handle member is preferably contoured to be gripped by the operating physician's assistant and is connected to the first elongate section at the distal end portion of the first elongate section, thus permitting one-handed use by the physician's assistant. The handle member permits the retractor to be lifted at any desired angle with respect to the surgical field. Thereafter a pulling force may be applied to the handle member so that a corresponding pulling or retraction force is applied to the tissue via the first elongate section. This force creates the space along the surgical field when the desired tissue or organ is drawn away from the tissue surrounding the target area. The handle member may also have an elongated rod extending from the opposite end portion of the handle member that allows the retractor to be maneuvered into the desired position by the physician's assistant and then fixed in the desired relative position by clamping or grasping the retractor with the available operating table retention mechanisms. As used herein, reference to the proximal end portion of an element is the end portion of an element that is spaced apart from the handle member and reference to the distal end portion of an element is the end portion of an element that is generally adjacent to or closer to the handle member of the preferred form of the present invention.

The first elongate section preferably has a first elongate proximal end portion, a first elongate distal end portion, a first elongate outer surface, and a first elongate inner surface. The first elongate section preferably functions to transfer to lifting and/or retention forces from the handle member to the tissue or organ of the patient. Similarly, the second elongate section, which may be substantially transparent, has a second elongate proximal end portion, a second elongate distal end portion, a second elongate outer surface and a second elongate inner surface.

The first elongate proximal end portion preferably has a generally blunt shape having a small lip member thereon that allows the retractor to be pushed into the surgical site and retain the desired tissue or organ. Additionally, the first elongate proximal end portion preferably includes a pair of tab members or similar retaining members thereon to retain the proximal end portion of the second elongate section therein. In the preferred form of the tab members, the proximal end portion of the second elongate section is insertable laterally into the tab members on the proximal end portion of the first elongate section. The tab members preferably extend outwardly a small distance beyond the face of the proximal end portion of the first elongate section. The face of the upper and proximal surfaces of the first elongate section is preferably slightly curved to provide a low profile that assists in the retention of the tissue while the lower and distally extending portion protects and retains the proximal end portion of the second elongate section therein. The sides of the first elongate section are also preferably slightly tapered so that the width of the first elongate section is less than the width of the first elongate section adjacent to the upper portion thereof.

The second elongate section preferably functions to perform the illumination feature of the present invention. The second elongate outer surface of the second elongate section is preferably slidable laterally with respect to a portion of the first elongate section and into engagement with the first elongate section such that the first and second elongate sections are substantially adjacent to each other and are generally aligned with each other. The retractor further includes a shield member along the distal end portion of the second elongate section to shield the user from the illumination from the second elongate section adjacent to the handle member.

The proximal end portion of the second elongate section preferably has a rounded shape or, alternatively, a smoothly radiused pointed shape. The shape of the second elongate section proximal end portion is preferably complementary to the shape of the recess between the tab members of the first elongate section proximal end portion so that the proximal end portion of the retractor, when the first and second elongate sections are connected, can readily retain and illuminate the tissue or organ along the surgical site as the retractor is inserted into the surgical site or field and maneuvered into position and so that the proximal end portion of the second elongate section is securely retained in the tab members with a relatively low side profile. Additionally, the proximal end portion of the second elongate section is also preferably configured to direct light forwardly of the retractor during use.

In order to enhance the reflective qualities of the illuminated retractor, the first elongate inner surface of the first elongate section may preferably include a mirrored surface thereon. Also, the second elongate inner surface of the second elongate section may preferably have a surface thereon that refracts the light forwardly at a desired angle. The mirrored surface of the first elongate inner surface and the surface of the second elongate inner surface function to minimize the light intensity loss of the light energy that is provided to the surgical field by the illuminated retractor. Alternately, the second elongate inner surface may be reflective to direct to the illumination outwardly from the second elongate outer surface. Furthermore, the second elongate section may be constructed so as to reflect to the illumination forwardly from the second elongate section to illuminate the tissue in the surgical site generally along the length of the illuminated surgical retractor. For example, the second elongate section may be formed so that the light is transmitted at a forward angle that is between about 15 and 75 degrees and more preferably between about 30 and 60 degrees relative to the second elongate section while also scattering the illumination to the sides along the first elongate section of the retractor as desired. Furthermore, although the preferred form of the second elongate section is a clear plastic or similar member, it is anticipated that various elements may be used such as light pipes, fiber optic panels or other available components that function to illuminate substantially the entire length of the retractor.

The preferred form of the retractor may also include a light shield along the upper portion of the first elongate section to shield the user from the illumination from the upper portion of the second elongate section and a connector between the handle member and the first and second elongate sections. This connector is preferably a twist type of connection between the second elongate section and the light cable. This connection is preferably simple to make, such as by a one-quarter turn, and is secure to ensure that the second elongate section remains attached to the first elongate section and the handle member as the retractor is inserted and the tissue or organ is retained by the physician's assistant. The connector also connects the light cable to the second elongate section to ensure that the light energy travels from the light source, through the connector and into the second elongate section. The light energy fills the second elongate section and turns the second elongate section into a "light pipe." The light energy is, in turn, radiated from the second elongate section into the surgical site exposed by the retractor. In this manner, light can be provided from the light source via the optical cable to the illumination input end portion of the second elongate section so that the second elongate section is illuminated, which results in an illuminated surgical field.

A further feature of the preferred form of the present invention is that the second elongate section may be replaceably mounted onto the first elongate section as desired to allow for the use of second elongate sections that direct light energy in a particular manner depending on the intended use of the retractor. A further feature of the preferred form of the present invention is the provision of a shielded portion along the illuminated retractor of the present invention. Additionally, at least a portion of the shaft shaped portion and/or the distal end portion of the second elongate section is preferably spaced apart from at least a portion of the distal end portion of the first elongate section and handle member to ensure that there is no heat buildup between these elements of the illuminated surgical retractor. Alternately, this portion of the second elongate section may be formed with a frosted coating to dissipate light therealong or may be coated to prevent the emission of light therefrom. Additionally, the use of a shield member also protects the distal end portion of the second elongate section and reduces the potential for damage to the surgical drape if the illuminated retractor is inadvertently left on and rested with the face of the retractor against the surgical drape for a short period of time.

BRIEF DESCRIPTION OF THE FIGURES OF THE DRAWINGS

Embodiments of the invention are described by way of example with reference to the accompanying drawings, in which.

DETAILED DESCRIPTION OF THE INVENTION

The present invention provides an illuminated retractor for illuminating the surgical field in a deep pelvic operation or similar surgical procedure, such OB/GYN procedures, and the adjacent tissue or organs when the illuminated retractor is used to retract the tissue or an organ away from the desired tissue or organ to be operated on.

As shown in the drawings, the present invention relates to an illuminated surgical retractor 10 having a handle member 20, a first elongate section 30, a second elongate section 40, and a first connector 31.

The handle member 20 is an elongate and generally cylindrical member that has a first top handle member end portion 22 and a second bottom handle member end portion 24. The second handle member end portion 24 of the handle member 20 is connected to the first elongate section 30 by the shaft portion 35 which is located distally of the distal end portion 32 on the first elongate section 30 to allow the handle member to be spaced apart from the surgical site to minimize the obstruction of the view of the surgical site by the physician's assistant and physician. The best combination of retractor mobility and application of retractive or pulling force occurs when the angle α between the handle member 20 and the first elongate section 30 is between about 45 and 175 degrees and more preferably between about 75 and 160 degrees. The handle member 20 permits the retractor 10 to be lifted or manipulated at nearly any angle with respect to the tissue or organ to be manipulated. Therefore, when a rearward or pulling force is applied to the handle member 20, a retractive force is applied to the tissue or organ via the first elongate section 30 to enlarge or provide a clear view of the surgical site. Application of this force causes the manipulation of the tissue or organ to allow the user to observe and perform the procedure free from obstruction by the manipulated tissue or organ.

Figures 1, 2:
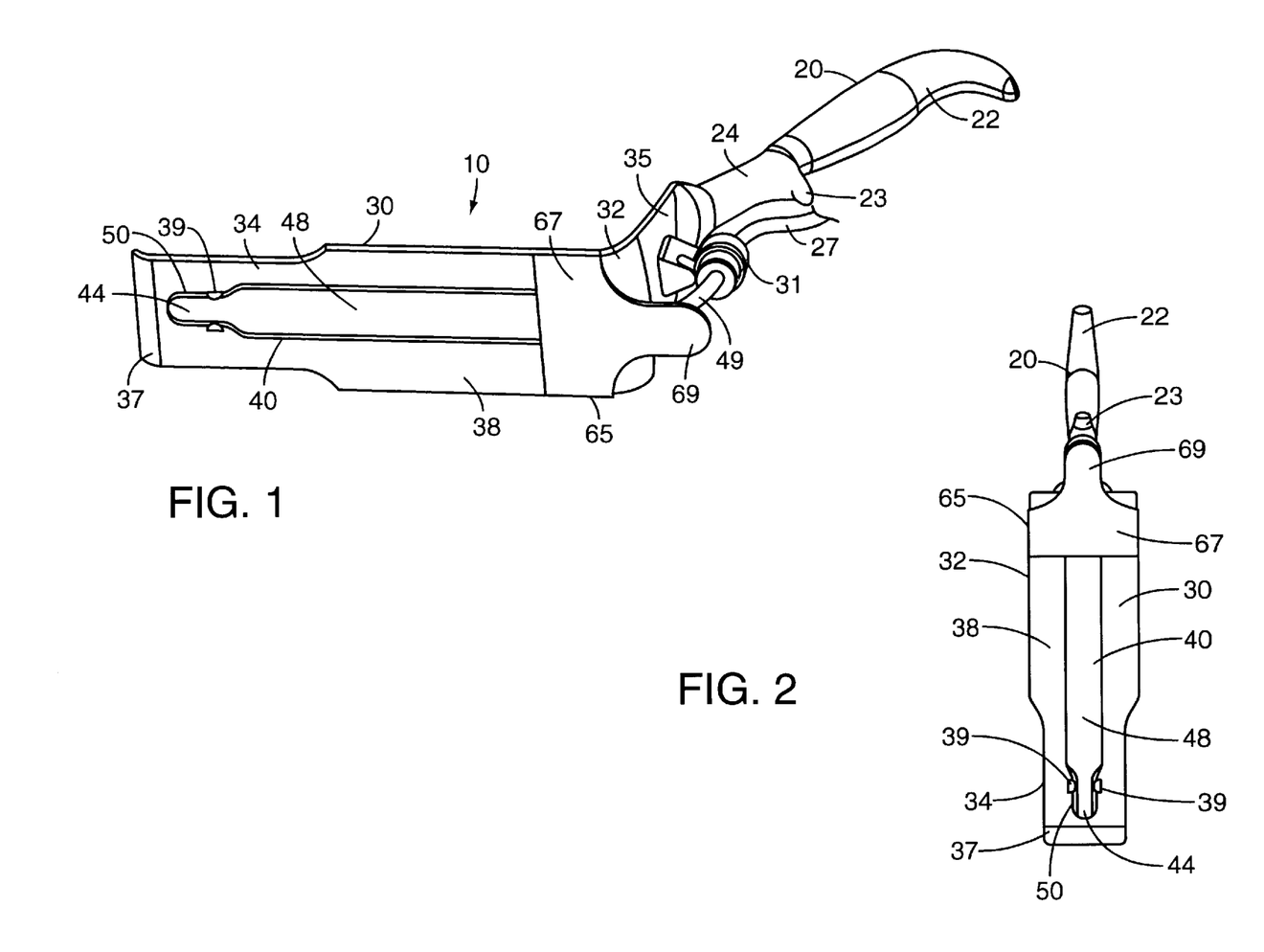
FIG. 1 is a perspective view of the preferred form of an illuminated retractor according to the present invention.
FIG. 2 is a front view of the preferred form of an illuminated retractor according to the present invention with the optical cable removed for clarity.
Figures 3, 4:
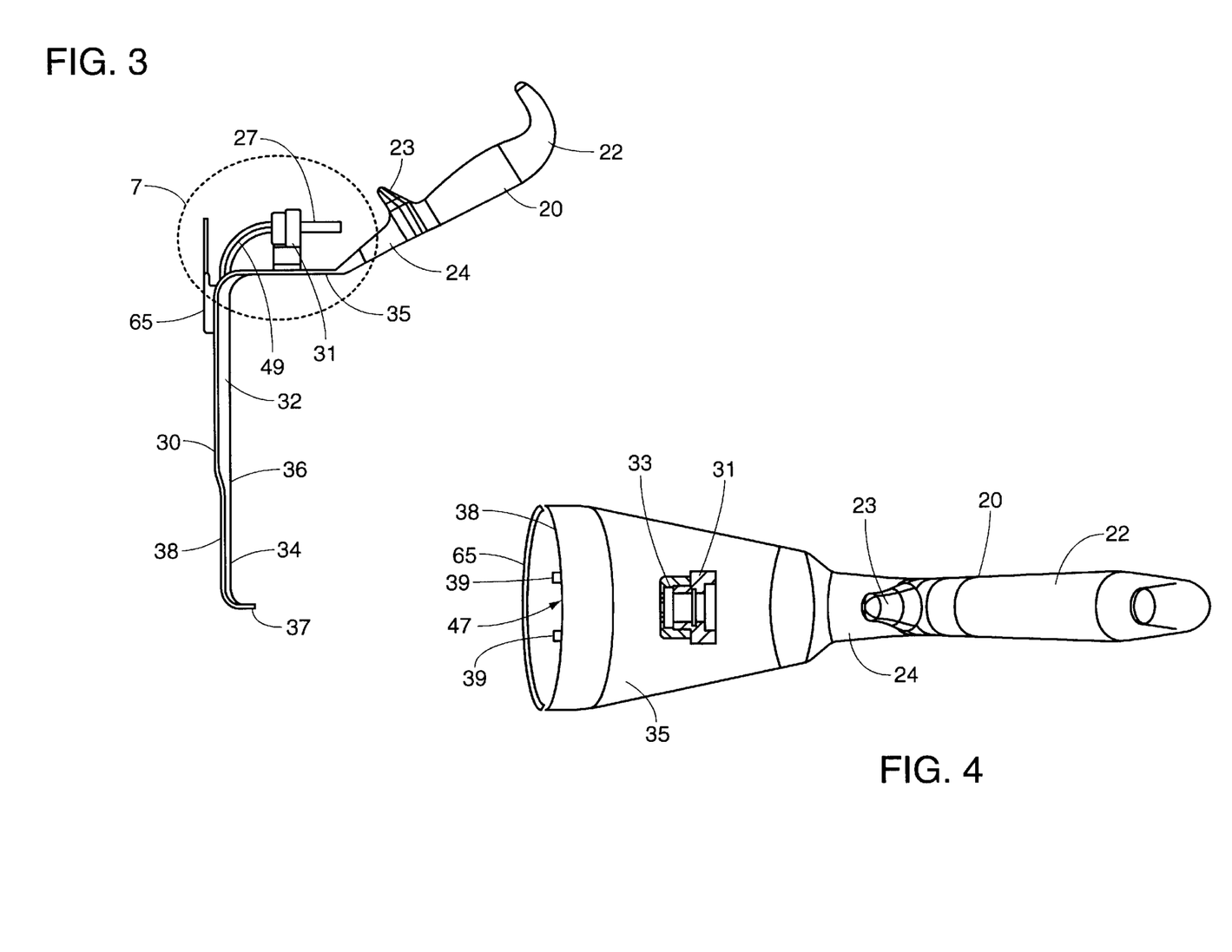
FIG. 3 is a side view of the preferred form of an illuminated retractor according to the present invention.
FIG. 4 is a top view of the preferred form of an illuminated retractor according to the present invention with the first connector in cross-section and the optical cable and second elongate section removed for clarity.
Figures 5, 6, 7:
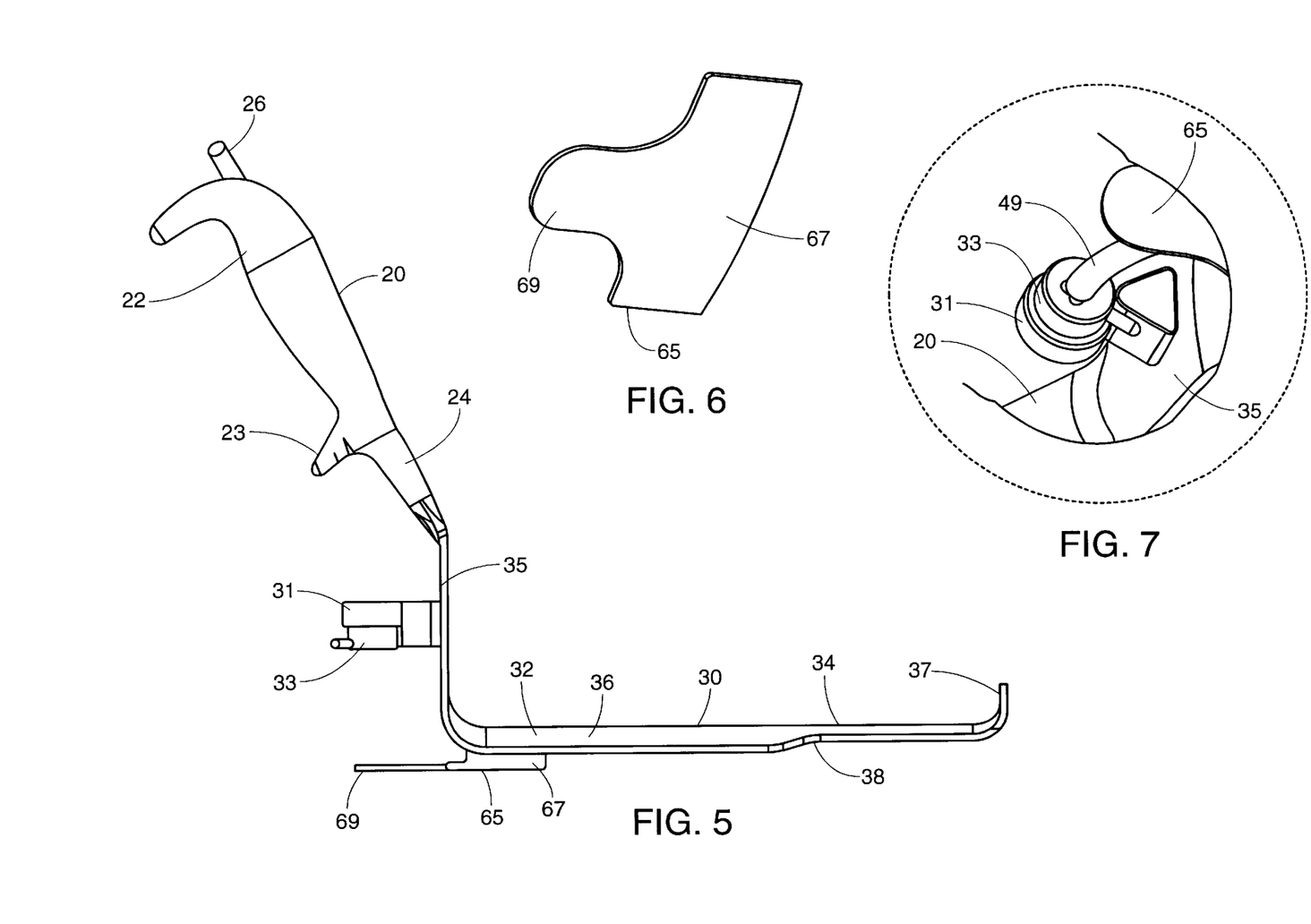
FIG. 5 is an enlarged side view of the preferred form of an illuminated retractor according to the present invention with the optical cable and second elongate section removed for clarity.
FIG. 6 is a perspective view of the shield member of the present invention.
FIG. 7 is an enlarged partial view of the connector and a portion of the second elongate section and shaft portion of the preferred form of an illuminated retractor according to the present invention taken generally along lines 7—7 of FIG. 3.
Figures 8A, 8B:
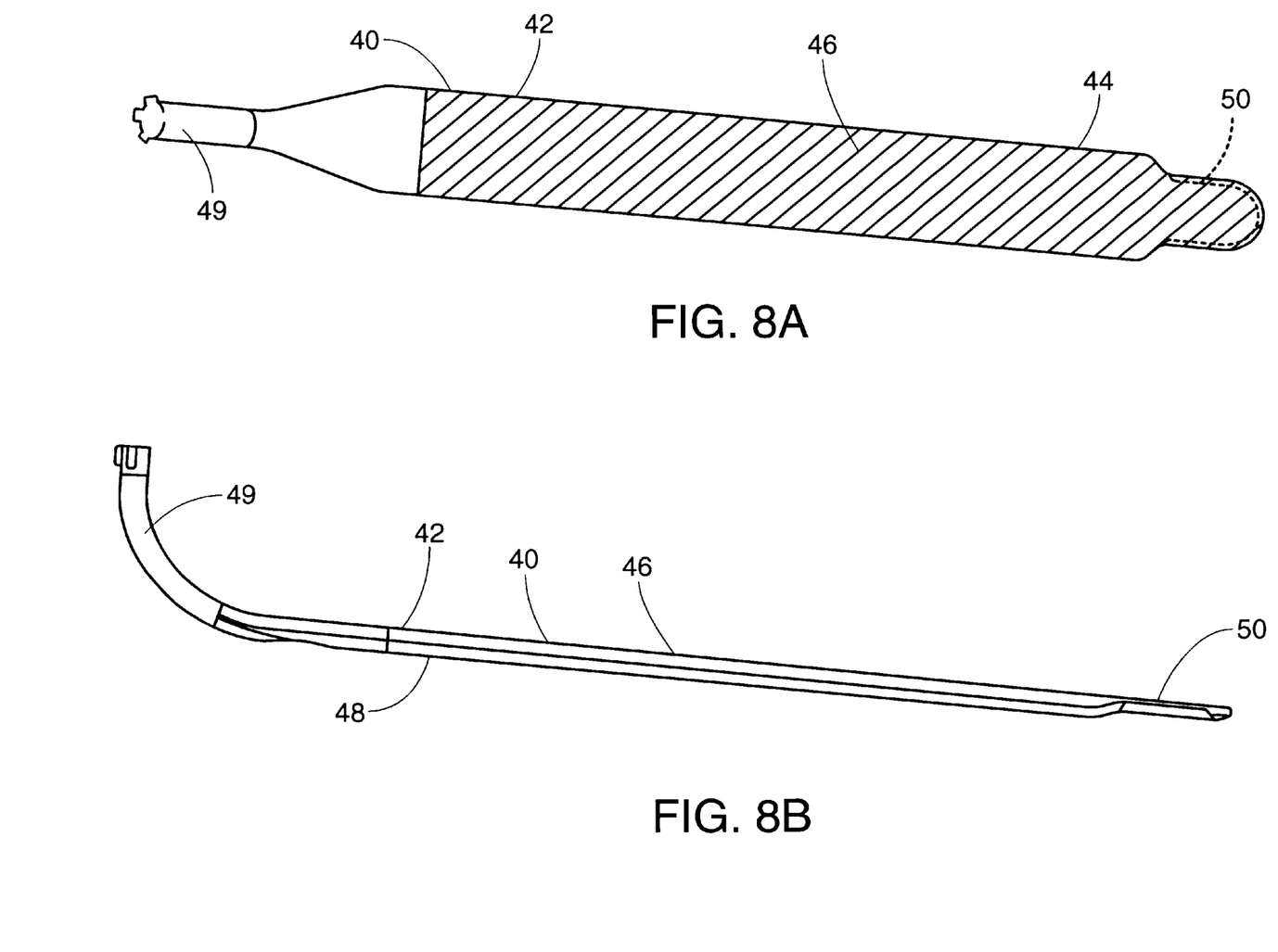
FIGS. 8A and 8B are perspective views of the preferred form of the second elongate section of the present invention.
Figure 9:
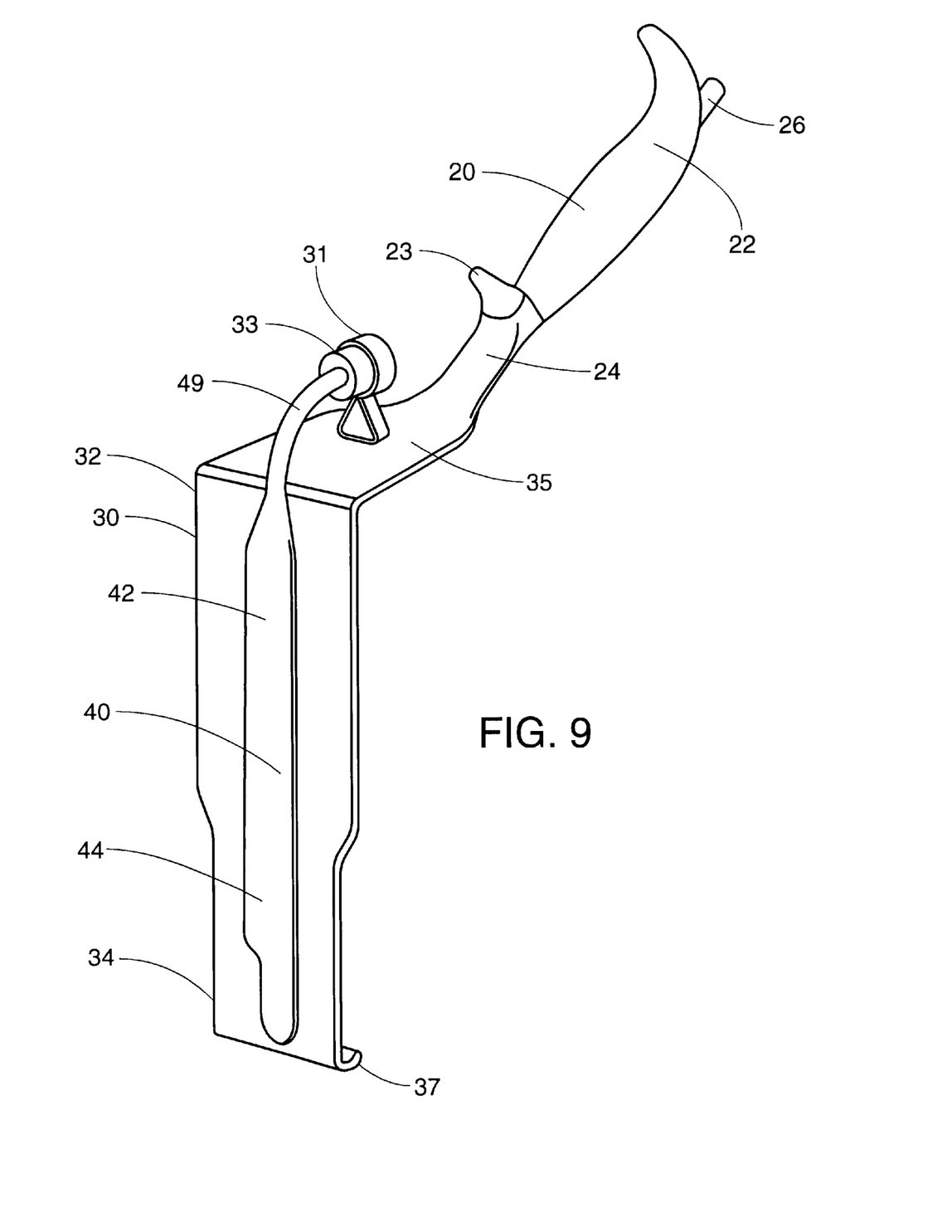
FIG. 9 is a perspective view of the preferred form of the present invention with the shield member and optical cable removed for clarity.

The handle member 20 of the retractor 10 also preferably includes a finger grip surface 23 that is preferably contoured to be gripped by the hand of the physician's assistant or physician to provide more tactile feel and feedback as well as increasing the comfort in using and maneuvering the retractor. The handle member 20 may also have an elongated rod 26 that extends outwardly from the first handle member end portion 22, as shown in FIG. 5. The elongated rod 26 allows the retractor 10 to be fixed or grasped by various operating table mechanisms known in the art so that the retractor 10 may be fixed in a desired position. These known operating table mechanisms are presently used to support various types of equipment around the surgical field and are typically attached at one end to the operating table and include one or more manipulable joints to allow the user to adjust the orientation of the medical device relative to the patient and the operative field. The use of the operating table mechanism and the elongated rod 26 allows the retractor 10 to be maneuvered into the desired position by the physician's assistant and then fixed in the desired relative position thus freeing both of the physician's assistant's hands to provide the desired surgical instruments of other assistance as requested by the physician. The elongate rod may also be used to connect the retractor to a chest or similar type of retractor that is used to open the surgical site by spreading the tissue of the patient.

The second handle member end portion 24 is preferably connected to the first elongate section 30 by the shaft portion 35. As shown, the handle member 20 is preferably connected to the shaft portion 35 and extends upwardly therefrom at an angle of about 30–45 degrees and the main portion of the handle member is preferably oriented relative to the first elongate section at an obtuse angle which is about 100–160 degrees. The shaft portion 35 is generally an extension of the handle member 20 and is preferably oriented generally perpendicular to the first elongate section at an angle of between about 75–105 degrees.

In the preferred form of the present invention, the shaft portion 35 is generally triangular in shape and increases in width from the handle member 20 to the first elongate section 30. The shaft portion 35 functionally forms part of the handle member and includes the first connector 31 extending upwardly therefrom to connect the second elongate section 40 to the optical cable 27 and provide for the transfer of light energy therethrough. Therefore, the orientation of the handle member relative to the first elongate section does not affect the connection between the optical cable 27 and the second elongate section 40 which occurs through the first connector 31. Although this connection between the handle member and the first elongate section is described herein as a rigid connection, it is anticipated that a pivotal connection may be used between the handle member and the shaft portion 35 or between the shaft portion and the first elongate section without affecting the operation of the optical cable and the second elongate section.

In the preferred form of the present invention, the first connector 31 allows for the releasable connection of the second elongate section 40 to the optical cable 27 in such a manner so as to allow for the transmission of light through the optical cable 27 and into the second elongate section 40. As shown, the first connector 31 preferably includes a key and keyway configuration that allows for the secure and quick connection of the second elongate section to the optical cable. Additionally, a preferred form of this connection includes the increase in resistance turning of these members and the secure positioning of the shaft shaped portion relative to the end of the optical cable. The second elongate section 40 may be quickly removed from the first connector 31 and the first elongate section 30 by rotating the connector knob 33 at least one-fourth turn relative to the handle member 20 to release the keys form the keyway. The use of the first connector 31 and the connector knob 33 allow the user to quickly and conveniently attach different second elongate sections to the handle member 20 and first elongate section 30 as desired. Although the preferred form of the connector between the optical cable 27 and the second elongate section 40 is described herein as a twist connector, it is anticipated that a variety of connections, such as bayonet, snap or threaded connections may be used, provided that the optical cable and shaft shaped member of the second elongate section are securely and operatively connected thereby.

The first elongate section 30 of the retractor 10 is preferably made of a rigid metal or similar material having sufficient strength to support the retracted tissue or organ during use. The first elongate section preferably has an elongate rectangular or blade shaped configuration with a cross section on the outer surface thereof that is slightly curved to assist in the retraction of the tissue or organ. The first elongate section also includes a first elongate proximal end portion 34, a first elongate distal end portion 32, a first elongate outer surface 36, a first elongate inner surface 38 and a lip portion 37 extending generally from and perpendicular to the first elongate proximal end portion 34. As shown in the drawings, the first elongate outer surface 36 and the first elongate inner surface 38 extend generally linearly from the proximal end portion 34 of the first elongate section 30 to a location near the distal end portion 32 of the first elongate section 30 and the width of the distal end portion is larger than the width of the proximal end portion.

The first elongate proximal end portion 34 preferably has a generally flat or blunt shape with a lip member 37 thereon. The lip member 37 is preferably oriented at a generally perpendicular angle to the first elongate section 30 and is shaped to allow the retractor 10 to be pushed into the surgical site and maneuvered to the desired location in the surgical site. As shown, the lip member 37 extends a short distance outwardly from the first elongate section to form a surface that assists in retaining the desired tissue or organ along the outer surface 36 of the first elongate section 30. Furthermore, the lip member 37 is oriented generally parallel to the shaft portion 35.

The inner surface 38 of the first elongate section 30 also preferably includes one or more tab members 39 thereon. As shown, the tab members 39 preferably form a second connector or receiving area 47 in combination with the first elongate inner surface. The receiving area 47 is shaped to receive and securely retain a portion of the proximal end portion of the second elongate section 40 therein.

Additionally, and as described in further detail below, the distal end portion of the first elongate section preferably includes a shield member 65 associated therewith to shield the user from the light emitted from the distal portion of the second elongate section 40 so that the light does not reflect into the user's eyes as the tissue or organ is retracted. The shield member 65 is preferably slightly arcuate and may be attached to the sides of the distal end portion so that the second elongate member may be slid between the first elongate section and the inner surface of the shield member as the second elongate section is mounted on the retractor. Alternately, the shield member may be pivotal along one side to allow for the direct mounting of the second elongate section onto the first elongate section or the shield member may be removable from the distal end portion of the first elongate section to allow the user to attach the shield member 65 onto the retractor as desired. As shown, the shield member 65 includes an elongate lower portion 67 that extends between the sides of the distal end portion of the first elongate section. The lower portion is spaced apart from the fist elongate section and may be fixedly or removably attached to the first elongate section to allow the distal end portion of the second elongate section to be positioned adjacent to the first elongate section. The upper portion 69 of the shield member preferably includes a raise portion that extends above the top of the first elongate section and preferably obstructs the user's view of the shaft portion of the second elongate section as well as the shaft portion 35 and first connector 31.

The second elongate section 40 has a second elongate proximal end portion 44, a second elongate distal end portion 42, a second elongate outer surface 46, a second elongate inner surface 48 and a shaft shaped portion 49. As shown in the drawings, the second elongate outer surface 46 is preferably and the second elongate inner surface 48 even more preferably are generally flat in cross section and extend from the proximal end portion 44 of the second elongate section 40 to near the distal end portion 42 of the second elongate section 40. More specifically, as the second elongate section 40 extends distally beyond the second elongate distal end portion 42, the second elongate section 40 tapers into a shaft shaped member 49 which then curves to match the curvature at the intersection of the shaft portion 35 of the first elongate section 30. This bend portion in the shaft shaped member 49 of the second elongate section 40 also allows the shaft shaped member 49 of the second elongate section 40 to be spaced apart from the inner surface 38 of the first elongate section 30 and the shaft portion 35 to reduce the potential for the buildup of heat on the retractor 10 from the light energy passing through the second elongate section. It is anticipated that this bend portion may include a "frosted" surface thereon to diffuse light energy thereon or may otherwise be coated to prevent the loss or escape of the light energy therefrom and to further reduce the glare from this portion of the illuminated retractor. The second elongate outer surface 46 and the second elongate inner surface 48 correspondingly are eliminated as the second elongate section 40 tapers into the shaft shaped member 49.

The second elongate section 40 is preferably an elongate and rectangular or blade shaped member, although it is anticipated that the second elongate section may also be formed as a single or multiple light fiber member. The second elongate section is also preferably substantially transparent and is made of a transparent plastic, such as a transparent acryl resin, which has the benefit of being highly resistant to breakage while retaining the ability to flex or deform under pressure and then return undamaged to the original, unstressed configuration. However, the second elongate section 40 may also be made of glass or other types of known substantially transparent material.

The second elongate outer surface 46 of the second elongate section 40 is configured such that the first and second elongate sections 30, 40 are preferably substantially parallel to each other along the substantial length of the first and second elongate sections 30, 40. The second elongate section 40 may be connected to the first elongate section 30 by inserting the second elongate proximal end portion 44 into the tab members 39 of the receiving area 47 while the second elongate member distal end portion and shaft shaped member 49 are inserted into the first connector 31 of the shaft portion 35 to securely retain the second elongate section adjacent to the first elongate section and engage the optical cable 27 with the second elongate section 40. The second elongate proximal end portion 44 may optionally include a lip member 50 thereon which is sized to be received in the receiving area 47 of the tab members 39.

Alternately, the second elongate section may be connected to the first elongate section in any manner known in the art that is within the level of ordinary skill of one in the surgical field. For example and less desirably than the embodiment described above, the second elongate outer surface 46 may be chemically bonded to the first elongate inner surface 38 through the use of an adhesive or by other chemical bonding means known to one skilled in the art. This chemical bonding may permanently affix the first and second elongate sections 30, 40 or may preferably allow the first and second elongate sections 30, 40 to be releasably connected for ease of sterilization of the respective elongate sections 30, 40. Alternately, if the second elongate section is a light fiber element, the light fiber element may be threaded through various retention members located along the lengthwise dimension of the first elongate section.

The second elongate proximal end portion 44 of the second elongate section 40 has a rounded shape or, alternatively, a smoothly radiused pointed shape. The shape of the second elongate proximal end portion 44 is sized to be securely received in the receiving area 47 of the tab members 39 and so that flexing of the first elongate section and second elongate section will not separate the second elongate section from the receiving area.

As described briefly above, the first elongate section 30 preferably has a slightly curved cross-sectional shape along the width dimension thereof. The curved cross-section of the first elongate section 30 causes the first elongate outer surface 36 to be convex. The convex cross-sectional shape of the first elongate outer surface 36 of the first elongate section 30 aids in the prevention of unnecessary trauma to the retracted tissue because the first elongate outer surface 36, which is in contact with the tissue or organ when the pulling force is applied to the retractor 10, presents no sharp edges that could cause tearing of the tissue or organ. Rather, the shape aids in distributing the force applied to the retracted tissue by the first elongate section 30. The first elongate inner surface 38 of the first elongate section 30 is preferably generally flat in cross section to further reinforce the first elongate section. Alternately, the first elongate inner surface may be generally concave in cross-section. The second elongate outer surface 46 of the second elongate section 40 may also preferably define a generally flat surface in cross-section that is complementary to the preferred cross-sectional shape of the inner surface 38 of the first elongate section 30. As will be obvious to one skilled in the art, if a complementary fit of the second elongate outer surface 46 of the second elongate section 40 and the inner surface 38 of the first elongate section 30 is desired, the outer surface 46 of the second elongate section 40 may have nearly any geometric cross-section that allows the second elongate outer surface 46 to complementarily fit against the inner surface 38 of the first elongate section 30, as there is no requirement that the first elongate inner surface 38 be concave in cross-section.

There is also no constraint requiring that the outer surface 46 of the second elongate section 40 be complementarily shaped to the inner surface 38 of the first elongate section 30. The only constraint on the shape of the geometric cross-section of the second elongate section 40 is that the chosen geometric cross-section should allow the second elongate section 40 to be preferably protected, by means known in the art, by the first elongate section 30 such that the first and second elongate sections 30, 40 are preferably operatively interconnected and complementary to each other. Even more preferably, the first and second elongate sections are substantially parallel to each other while also providing the optimal and desired illumination for the procedure. As shown, the width of the first elongate section 30 is preferably significantly greater than the width of the second elongate section, although the relative width of each component may be varied depending on the amount and location of the illumination that is desired by the user.

In order to enhance the reflective qualities of the retractor 10, the first elongate inner surface 38 of the first elongate section 30 preferably has a mirrored or reflective surface. Also, the second elongate inner surface 48 of the second elongate section 40 preferably has a surface to refract the light in the desired direction or directions. The mirrored surface of the first elongate inner surface 38 and the surface of the second elongate inner surface 48 act to minimize the loss of the light intensity that is provided to the surgical field by the illuminated retractor 10. Alternately, the second elongate inner surface may include a reflective coating or other surface thereon to reflect the light generated through the second elongate section outwardly through the second elongate outer surface 46. Additionally, the second elongate section may be formed so as to specifically direct the light forwardly or towards the proximal end of the retractor to direct the illumination forwardly beyond the lip portion 37 thereby assisting the user to illuminate the area of interest. Because the second elongate section of the present invention is readily removable, it is anticipated that a variety of second elongate sections may be used, including second elongate sections that are formed to direct the illumination forwardly and/or to one or both sides of the retractor as desired by the user. As shown, the illumination from the retractor is preferably at an angle of about forty-five degrees forwardly of the retractor, although this forward orientation of the light may be oriented to be between thirty degrees and ninety degrees with respect to the lengthwise dimension of the retractor. Similarly, the second elongate section may be formed to direct light sideways from the retractor at an angle of between about fifteen degrees and ninety degrees and more preferably about 45 degrees with respect to the retractor.

The light energy passes from the light source, through the optical cable 27 and enters the second elongate section at the end portion of the shaft shaped member 49 adjacent to the first connector 31. The shaft shaped member 49 of the second elongate section 40 directs the illumination to the second elongate distal end portion 42 of the second elongate section 40 and allows light energy to enter the second elongate section 40. The light energy fills the second elongate section 40, turning the second elongate section 40 into a "light pipe." The light energy is, in turn, radiated from the second elongate section 40, and particularly from the inner surface 48 of the second elongate section 40 between the distal end portion and proximal end portion of the second elongate section. The light is then directed into the surgical site exposed by the retractor 10. Since substantially the entire length of the second elongate section 40 is preferably illuminated, a large, well illuminated surgical field extends the substantial length of the second elongate section 40 of the retractor 10.

The first connector 31 releasably couples the optical cable 27 to the shaft shaped member 49 of the second elongate section 40. The first connector 31 is adapted to receive and releasably retain the shaft shaped member 49 of the second elongate section therein to couple the shaft shaped member 49 to the optical cable 27. In this manner, light can be provided from the light source via the optical cable to the shaft shaped member 49 of the second elongate section 40 so that the second elongate section 40 is illuminated.

The present invention has been described in reference to use in retracting or retaining tissue or organs adjacent to a surgical site or surgical field. It would be obvious to one skilled in the art that the present invention could also be used in other procedures in which the illumination of the surgical field is desired. Furthermore, although the present invention has been described with reference to specific details of the preferred embodiments thereof, it is not intend that such detail should be regarded as limitations upon the scope of the invention except as and to the extent that they are included in the accompanying claims.

What is claimed is:

1. An illuminated surgical retractor comprising:
   a handle member having a first handle end portion and a second handle end portion;
   a shaft portion interconnected with said second handle end portion;
   a first elongate section having a lengthwise dimension and a first elongate proximal end portion, a first elongate distal end portion, and a first elongate inner surface extending from the first elongate proximal end portion to near the first elongate distal end portion, the shaft portion operatively connected to the first elongate distal end portion of said first elongate section such that said handle member forms an obtuse angle with said first elongate section;

a second elongate section having a lengthwise dimension and a second elongate proximal end portion, a second elongate distal end portion and a second elongate outer surface extending from the second elongate proximal end portion to near the second elongate distal end portion, and a second elongate inner surface extending from the second elongate proximal end portion to near the second elongate distal end portion, said second elongate section being generally aligned with the lengthwise dimension of the first elongate section such that said first and second elongate sections are substantially parallel, said second elongate section defining an illumination output portion; and said shaft portion having a connector associated therewith and said connector couples the second elongate section to a source of illumination so that said second elongate section is illuminated substantially along the length thereof.

2. The illuminated surgical retractor of claim 1, wherein the shaft portion is generally oriented perpendicular to the first elongate section.

3. The illuminated surgical retractor of claim 2, wherein said shaft portion supports a connector that engages at least a portion of said second elongate section.

4. The illuminated surgical retractor of claim 1, wherein at least a portion of said second elongate section is engaged by at least a portion of said first elongate section.

5. The illuminated surgical retractor of claim 1, wherein the first elongate section includes a shield member thereon and said shield member shields at least a portion of the illumination from said second elongate section therein.

6. An illuminated surgical retractor for use in a patient comprising:

a handle member having a first handle end portion and a second handle end portion;

a first elongate section having a first elongate proximal end portion with a lip member thereon, a first elongate distal end portion, and a first elongate inner surface extending from the first elongate proximal end portion to near the first elongate distal end portion, the second handle end portion of said handle member interconnected with said first elongate section such that said handle member forms an obtuse angle with said first elongate section;

a second elongate section having a second elongate proximal end portion, a second elongate distal end portion and a second elongate outer surface extending from the second elongate proximal end portion to near the second elongate distal end portion, and a second elongate inner surface extending from the second elongate proximal end portion to near the second elongate distal end portion, said second elongate section connected to said first elongate section such that said first and second elongate sections are substantially aligned, the second elongate distal end portion of said second elongate section defining an illumination output member; and a shield member associated with the distal end portion of the first elongate section wherein the shield member forms an area between the shield member and the first elongate section for the receipt of at least a portion of the second elongate section therein.

7. The illuminated surgical retractor of claim 6, wherein said handle member has an elongated rod extending from the handle member and wherein elongate rod is sized to be engaged by an operating table mechanism to retain the retractor in a desired position relative to the patient.

8. The illuminated surgical retractor of claim 6, wherein said handle member is operatively connected to said first elongate section by a shaft portion.

9. The illuminated surgical retractor of claim 8, wherein said first elongate section is oriented at a generally perpendicular angle relative to the shaft portion.

10. The illuminated surgical retractor of claim 8, wherein said shaft portion further includes a connector thereon for releasably receiving and optically coupling the second elongate section to a source of illumination.

11. The illuminated surgical retractor of claim 8, wherein a connector enables said second elongate section to be removable from the first elongate section.

12. The illuminated surgical retractor of claim 6, wherein said shield member is oriented at an obtuse angle with respect to said handle member.

13. The illuminated surgical retractor of claim 12, wherein said shield member is generally parallel to said first elongate section.

14. The illuminated surgical retractor of claim 6, wherein at least a portion of said second elongate section is surrounded by at least a portion of said first elongate section.

15. The illuminated surgical retractor of claim 6, wherein said at least a portion of second elongate section is positioned between said shield member and said first elongate section.

16. The illuminated surgical retractor of claim 6, wherein at least a portion of said first elongate section substantially surrounds at least a portion of said second elongate section and said at least a portion of said second elongate section is removable therefrom.

17. The illuminated surgical retractor of claim 6, wherein said second elongate section is laterally insertable into engagement with said first elongate section.

18. The illuminated surgical retractor of claim 9, wherein said first elongate section is fixedly positioned with respect to said handle member and said second elongate section is removable therefrom.

19. An illuminated surgical retractor comprising:

a handle member having a first handle end portion and a second handle end portion and at least a portion thereof that is illuminated in use;

a shaft portion connected to the second handle end portion and said shaft portion having a connector thereon;

a first elongate section having a first elongate proximal end portion with a lip member thereon, a first elongate distal end portion, and a first elongate inner surface extending from the first elongate proximal end portion to near the first elongate distal end portion, the second handle end portion of said handle member interconnected to the first elongate distal end portion of said first elongate section by said shaft portion such that said handle member forms an obtuse angle with said first elongate section;

a second elongate section having a second elongate proximal end portion, a second elongate distal end portion, and a second elongate outer surface extending from the second elongate proximal end portion to near the second elongate distal end portion, and a second elongate inner surface extending from the second elongate proximal end portion to near the second elongate distal end portion, the second elongate distal end portion of said second elongate section defining an illumination output member; and the shaft portion is oriented generally parallel to the lip member on the first elongate proximal end portion.

20. The illuminated surgical retractor of claim 19, wherein the second elongate section is substantially illuminated along the length thereof.

21. The illuminated surgical retractor of claim 19, wherein said second elongate section includes a shaft shaped portion that is at least partially shielded by a shield member associated with the distal end portion of the first elongate section.

22. The illuminated surgical retractor of claim 19, wherein said first elongate section is fixedly retained with respect to said handle member.

23. The illuminated surgical retractor of claim 19, wherein the obtuse angle formed between said handle member and said first elongate section is from about 110° to 175°.

24. An illuminated surgical retractor comprising:

a handle member having a first handle end portion and a second handle end portion and a shaft portion extending from the second handle end portion thereof;

a first elongate section having a first elongate proximal end portion and a first elongate distal end portion with a first elongate inner surface extending between the first elongate proximal end portion and the first elongate distal end portion and said second handle end portion of said handle member is interconnected to said first elongate section;

a lip member extending from the first elongate proximal end portion and said lip member extends in generally the same direction as the shaft portion;

a second elongate section having a second elongate proximal end portion and a second elongate distal end portion with a second elongate outer surface extending between the second elongate proximal end portion and the second elongate distal end portion, a second elongate inner surface extending between the second elongate proximal end portion and the second elongate distal end portion, the second elongate distal end portion of said second elongate section defining an illumination input end portion;

a connector on said shaft portion releasably coupling the illumination input end portion to an optical cable.

25. The illuminated surgical retractor of claim 24, wherein said second elongate section is oriented at an obtuse angle with respect to said handle member.

26. The illuminated surgical retractor of claim 24, wherein at least a portion of said second elongate section is engaged by at least a portion of said first elongate section.

27. The illuminated surgical retractor of claim 24, wherein said first elongate section includes a shield member thereon and said shield member obstructs the illumination from at least a portion of said second elongate section.

28. The illuminated surgical retractor of claim 24, wherein said second elongate section forms a light pipe and includes a surface thereon for directing light forwardly therefrom.

29. An illuminated surgical retractor for retracting tissue in a surgical site and illuminating the adjacent tissue of a patient, the retractor comprising:

a handle member having a first handle end portion and a second handle end portion with a gripping area therebetween for gripping by the user and an optical cable extending therealong;

a shaft portion associated with the second handle member end portion and including a connector thereon;

an elongate first elongate section sized to be positioned in the surgical site to retract tissue therein and having a first elongate proximal end portion with a lip member thereon and a first elongate distal end portion with a first elongate inner surface extending between the first elongate proximal end portion and the first elongate distal end portion, the second handle end portion of said handle member interconnected to the first elongate section;

an elongate second elongate section having a second elongate proximal end portion and a second elongate distal end portion with a second elongate outer surface extending generally parallel to said first elongate section and between the second elongate proximal end portion and the second elongate distal end portion and a second elongate inner surface extending between the second elongate proximal end portion and the second elongate distal end portion, the second elongate section further including an illumination input end portion thereon and at least a portion of said illumination input end portion is releasably engaged by said connector to optically coupling the illumination input end portion to the optical cable;

the first elongate section is oriented at an obtuse angle relative the handle member and said shaft portion is oriented generally parallel to said lip member; and wherein at least a portion of said second elongate section is releasable from said first elongate section and wherein said distal end portion of the first elongate section includes a shield member thereon and said distal end portion of said second elongate section is removable therefrom.

30. The illuminated surgical retractor of claim 29, wherein said second elongate section is formed to direct light laterally therefrom and beyond the first elongate section.

* * * * *